(12) United States Patent
Tripathi

(10) Patent No.: US 11,819,274 B2
(45) Date of Patent: Nov. 21, 2023

(54) NON-CONTACT WIDE ANGLE RETINA VIEWING SYSTEM

(71) Applicant: ALCON INC., Fribourg (CH)

(72) Inventor: Ashok Burton Tripathi, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 401 days.

(21) Appl. No.: 17/116,912

(22) Filed: Dec. 9, 2020

(65) Prior Publication Data
US 2022/0175241 A1 Jun. 9, 2022

(51) Int. Cl.
*A61B 3/13* (2006.01)
*A61B 3/00* (2006.01)

(52) U.S. Cl.
CPC .......... *A61B 3/0066* (2013.01); *A61B 3/0025* (2013.01); *A61B 3/13* (2013.01)

(58) Field of Classification Search
CPC ....... A61B 3/0066; A61B 3/0025; A61B 3/13; A61B 3/14; G02B 21/0012; G02B 21/241
See application file for complete search history.

(56) References Cited

U.S. PATENT DOCUMENTS

| | | | |
|---|---|---|---|
| 2005/0117207 A1 | 6/2005 | Haisch | |
| 2005/0225848 A1* | 10/2005 | Kirchhuebel | A61B 3/13 359/368 |
| 2009/0219483 A1* | 9/2009 | Takanashi | G02B 21/0012 359/813 |
| 2009/0244485 A1* | 10/2009 | Walsh | A61B 3/111 351/221 |
| 2012/0016349 A1* | 1/2012 | Brownell | A61F 9/009 606/4 |
| 2013/0144743 A1* | 6/2013 | Pugh | G01M 11/0278 705/26.1 |
| 2018/0333049 A1 | 11/2018 | Charles | |

FOREIGN PATENT DOCUMENTS

| | | | | |
|---|---|---|---|---|
| DE | 102017110816 A1 | * | 7/2018 | |
| EP | 3524136 A1 | | 8/2019 | |
| JP | 2009205156 A | * | 9/2009 | ............. A61B 3/132 |

* cited by examiner

*Primary Examiner* — George G. King
*Assistant Examiner* — Anna Elizabeth Smith
(74) *Attorney, Agent, or Firm* — Quinn IP Law

(57) ABSTRACT

A retina viewing system and method of using the same includes an ophthalmic microscope, a disposable lens attachment, and an electronic control unit (ECU). The microscope has an optical head and a set of internal focusing lenses, the latter providing the microscope with a variable working distance or focal length. The disposable lens attachment includes a resilient body with a proximal end connected to the optical head and a distal end connected to a high-power/high-diopter distal lens. The ECU executes instructions for viewing a retina or other intraocular anatomy of a patient eye. Execution of the instructions causes the ECU to automatically adjust the variable working distance or focal length of the microscope when viewing an image of the retina through the distal lens.

20 Claims, 4 Drawing Sheets

NON-CONTACT WIDE ANGLE RETINA VIEWING SYSTEM

INTRODUCTION

The present disclosure relates to automated systems and methods for visualizing the retina and other anatomy of a patient's eye when performing an ophthalmic procedure. The intraocular volume of a human eye is occupied by a transparent gel-like matter referred to as the vitreous body. The retina covers posterior walls of an internal cavity of the eye, i.e., the vitreous cavity, and thereby forms a thin layer of interconnected nervous tissue. Light entering the eye passes through the cornea and lens capsule, with zonules and ciliary muscles acting on the lens capsule to focus the admitted light onto the retina. Individual rod and cone photoreceptor cells of the retina react to the admitted light by generating nerve impulses, which in turn are interpreted by the brain as colors and images. Proper eyesight therefore depends on a healthy retina and viscous body.

Factors such as injury, age, and severe myopia can cause the vitreous body to separate from the retina. Resulting transient or sustained tension on the retina by the separating vitreous body may cause a tear in the retina. Likewise, blunt force to the eye or surrounding regions of the head can directly damage the retina. In order to properly diagnose retinal tears, vitreous detachment, and other intraocular conditions, a clinician typically employs a high-definition retina viewing system. Such a system illuminates the vitreous cavity with light in an eye-safe portion of the electromagnetic spectrum, and thereafter presents the illuminated anatomy under high magnification. In this manner, the clinician is afforded a clear view of the retina, macula, vitreous body, and other surrounding tissue. Similar magnification levels and high-definition viewing may be employed in pre-operative and post-operative diagnostic settings.

SUMMARY

Disclosed herein are an improved retina viewing system and an accompanying method for viewing the retina and other intraocular anatomy of a human eye. The present system is intended to provide a lower cost, non-contact, wide-angle retina viewing solution that eliminates the requirement for manual external focusing control of an accompanying ophthalmic microscope. Additionally, aspects of the present disclosure may use digital bar coding/serialization or another logic-based automation sequence to prevent inadvertent reuse of single-use disposable components of the retina viewing system as set forth below.

The retina viewing system according to an exemplary embodiment includes an ophthalmic microscope having an optical head, a disposable lens attachment having a high-power/high-diopter distal lens, and an electronic control unit (ECU). A proximal end of the disposable lens attachment is configured to connect to the optical head of the microscope, e.g., via magnetic attraction, hook-and-loop connection, adhesives, or direct mechanical engagement. The ECU, which is in communication with the microscope, is programmed to execute instructions for viewing the retina or other intraocular anatomy through operation of the distal lens and the microscope during an ophthalmic procedure.

The ophthalmic microscope contemplated herein, which may be digital or analog in different embodiments, includes a set of internal focusing lenses that collectively provide the microscope with a variable working distance or focal length. This feature stands in contrast to typical ophthalmic microscopes of the type characterized by a non-adjustable/fixed working distance, thus necessitating reducing lenses and a clinician's manual involvement in an external focusing action. The ECU, when informed by the spatial position and power of the distal lens disposed at a distal end of the disposable lens attachment, automatically controls a focal setting of the internal focusing lenses. The ECU may perform this adjustment automatically in some embodiments, i.e., without intervention or action by the clinician, thus providing an "auto-focus" capability. Such optional auto-focusing control occurs after the disposable lens attachment has been securely connected to the optical head. Alternatively, the ECU may act as a local controller providing control inputs in response to control inputs from the clinician, e.g., operation of a foot pedal.

A method is also disclosed for controlling the retina viewing system during an ophthalmic procedure on a patient eye. According to a disclosed exemplary embodiment, the method includes, in response to receiving of an initiation signal by the ECU, automatically verifying a connection of a proximal end of a disposable lens attachment to an optical head of an ophthalmic microscope. As summarized above, the microscope contemplated herein includes a set of internal focusing lenses providing the microscope with a variable working distance or focal length. A distal end of the disposable lens attachment is connected to a high-power/high-diopter distal lens.

In this embodiment, and in response to verifying the connection of the proximal end, the ECU adjusts the variable working distance or focal length of the ophthalmic microscope, autonomously or in response to control inputs from the clinician, to thereby view an image of a retina of the patient eye through the distal lens using the microscope.

The disposable lens attachment in a particular non-limiting configuration includes a high-power/high-diopter distal lens having refractive power of about 70 diopters to about 110 diopters, and a conical resilient body. The resilient body has a proximal end configured to connect to the optical head of an ophthalmic microscope, and a distal end connected to the distal lens. The conical resilient body is constructed of a resilient material configured to bend and/or collapse away from the patient eye in the event of contact therewith.

The above-described features and advantages and other possible features and advantages of the present disclosure will be apparent from the following detailed description of the best modes for carrying out the disclosure when taken in connection with the accompanying drawings.

DETAILED DESCRIPTION

Figure 1:
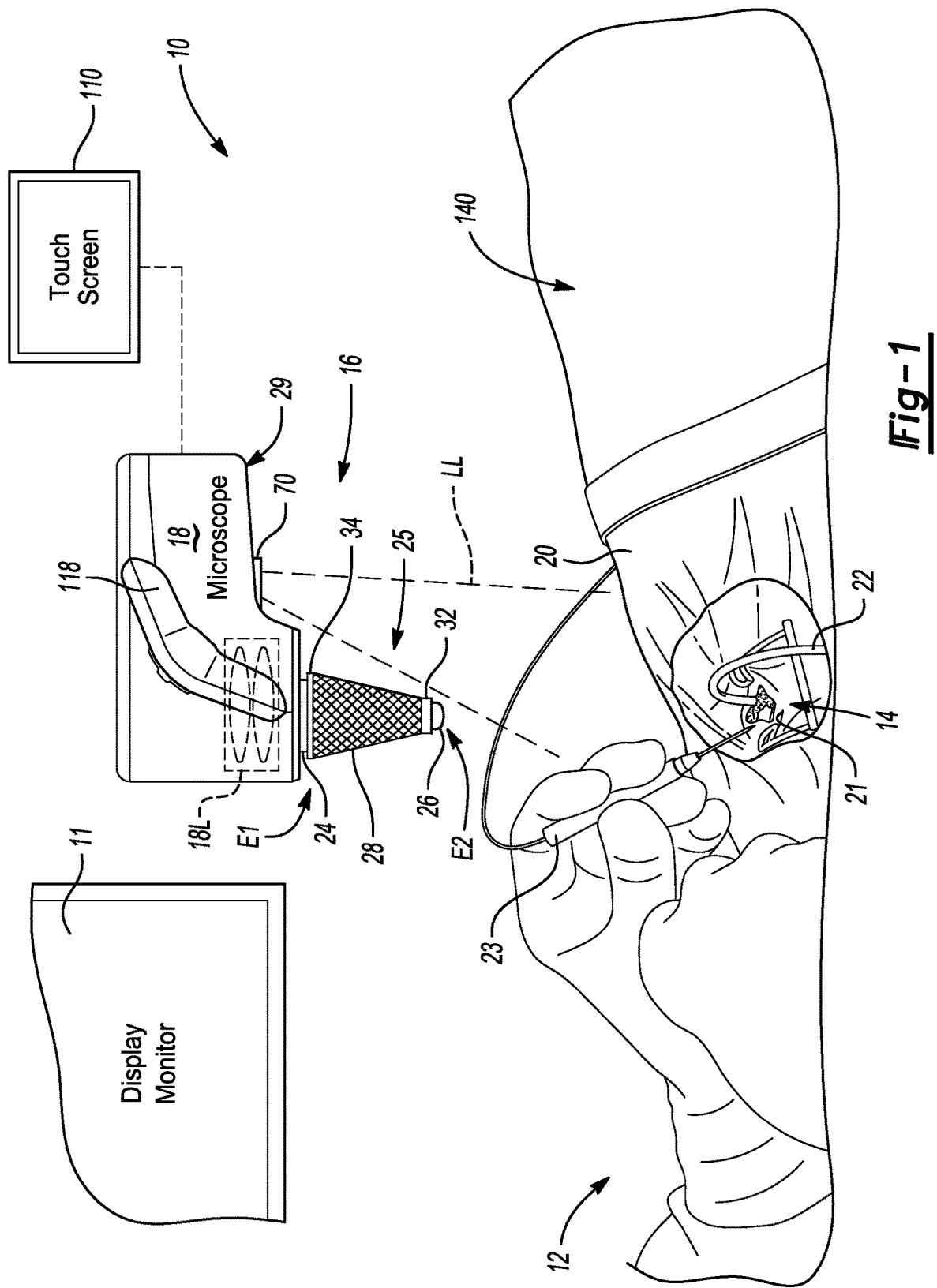
FIG. 1 is a schematic illustration of an exemplary ophthalmic procedure conducted using a retina viewing system constructed with a disposable non-contact lens attachment device in accordance with the present disclosure.

Embodiments of the present disclosure are described herein. It is to be understood, however, that the disclosed embodiments are merely examples, and that other embodiments can take various and alternative forms. The Figures are not necessarily to scale. Some features may be exaggerated or minimized to show details of particular components. Therefore, specific structural and functional details disclosed herein are not to be interpreted as limiting, but merely as a representative basis for teaching one skilled in the art to variously employ the present disclosure.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference, which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Referring to the drawings, wherein like reference numbers refer to like components, a representative ophthalmic procedure 10 is shown schematically in FIG. 1, during which a clinician 12 is required to precisely visualize the retina or other intraocular tissue within an eye 14 of a patient 140. To that end, the clinician 12 is assisted by high-definition multi-dimensional digital viewing capabilities of a retina viewing system 16, with the retina viewing system 16 constructed and controlled as set forth herein. For illustrative clarity, only select components of the retina viewing system 16 are depicted in FIG. 1, with the retina viewing system 16 described in greater detail below with reference to the remaining Figures.

As described below with reference to FIGS. 2 and 3, the retina viewing system 16 utilizes resident internal focusing capabilities of an ophthalmic microscope 18, e.g., a digital or analog medical-grade microscope, to provide a lower-cost, disposable, non-contact option for wide-angle retina viewing. At least some of the attendant benefits of the present teachings include the provision of high-power magnification during the course of the exemplary ophthalmic procedure 10 of FIG. 1 without the need for the clinician 12 to perform external focusing actions and without reducing lenses, or at least reducing the reliance of the clinician 12 on such external focusing actions and hardware. Specific control methodologies are disclosed herein with reference to FIG. 5 for providing improved optical clarity, ease of use, and serialization/traceability.

In a representative embodiment, the ophthalmic procedure 10 depicted schematically in FIG. 1 may be a vitreoretinal surgery or any other procedure related to the diagnosis and treatment of disease and/or damage to the intraocular anatomy of the eye 14. By way of example and not limitation, such a procedure 10 may encompass the direct repair or reattachment of a torn or separated retina, the performance of a vitrectomy, and/or the diagnosis and/or repair of a myriad of other possible conditions of the eye 14. Visualization of the target tissue during the course of the procedure 10 may be enhanced by real-time video broadcasting via a display monitor 11, such as a medical grade 4K or other ultra-high definition liquid crystal display (LCD) or organic light-emitting diode (OLED) panel, which is situated within easy view of the clinician 12 and other attending personnel within the surgical suite.

In preparation for the ophthalmic procedure 10, the patient 140 may be covered by a sterile surgical drape 20, with the drape 20 or another covering defining an opening 21 exposing the eye 14. A wire speculum 22 or other suitable tool may be used to retain the eye 14 in an open state during the procedure 10, during which the clinician 12 may insert a procedure-specific surgical tool 23 into the above-noted vitreous cavity. Depending on the nature or particular stage of the procedure 10, the surgical tool 23 may be variously embodied as forceps, a bladed vitrectomy probe, a cannula, an infusion tool, an endoilluminator, or any other surgical tool 23 that may be required.

As part of the present approach, the retina viewing system 16 is configured for magnifying and clearly visualizing the intraocular anatomy of the eye 14 in real-time so as to aid the clinician 12 and other attending personnel in conducting the ophthalmic procedure 10. To that end, the ophthalmic microscope 18 of the retina viewing system 16 may be suspended from overhead, e.g., connected to and/or supported by a multi-axis robot 30 (see FIG. 2). In order to function as intended with the retina viewing system 16 within the scope of the disclosure, the microscope 18 has a variable as opposed to a fixed working distance, and thus has a variable or adjustable focal length. A task light 70 arranged on an underside 29 of the microscope 18 or on another suitable surface may provide overhead lighting LL to further illuminate the eye 14 and the surrounding working space.

Those skilled in the art will appreciate that current non-contact, wide-angle disposable retina viewing systems typically utilize fixed-distance microscopes, and thus rely on external focus control attended to by the clinician 12. For instance, a rotary dial or knob may be rotated manually or via a surgeon-controlled servomotor to bring the retina into proper focus. A reducing lens used in such systems is typically disposed above patient's cornea, e.g., 150 mm to 175 mm away. Due to the fixed working distance noted above, the reducing lens is moved via manipulation by the clinician 12 of the above-noted knobs and/or by operation of a footswitch to bring the retina into a desired focus.

In contrast, the retina viewing system 16 of the present disclosure reduces and possibly eliminates the need for external focusing and the reducing lens. This in turn eliminates a potentially problematic feature that at times can be unstable, and that requires additional dexterity and operating time. For instance, disclosed embodiments of the retina viewing system 16 eliminate the above-noted reducing lens, as well as the need for external focusing thereof, although the use of a reducing lens is not strictly precluded in the event a particular clinician 12 prefers to retain this option. Performance advantages are thus provided via integration of direct or indirect focus control of a set of internal focusing lenses 18L of the ophthalmic microscope 18 with other aspects of the retina viewing system 16. That is, the present approach taps into and harnesses the focusing capabilities of the ophthalmic microscope 18, for instance digital embodiments thereof, to provide a lower cost disposable option for retina viewing, one that greatly simplifies and enhances vitreoretinal surgical procedures.

Figure 2:
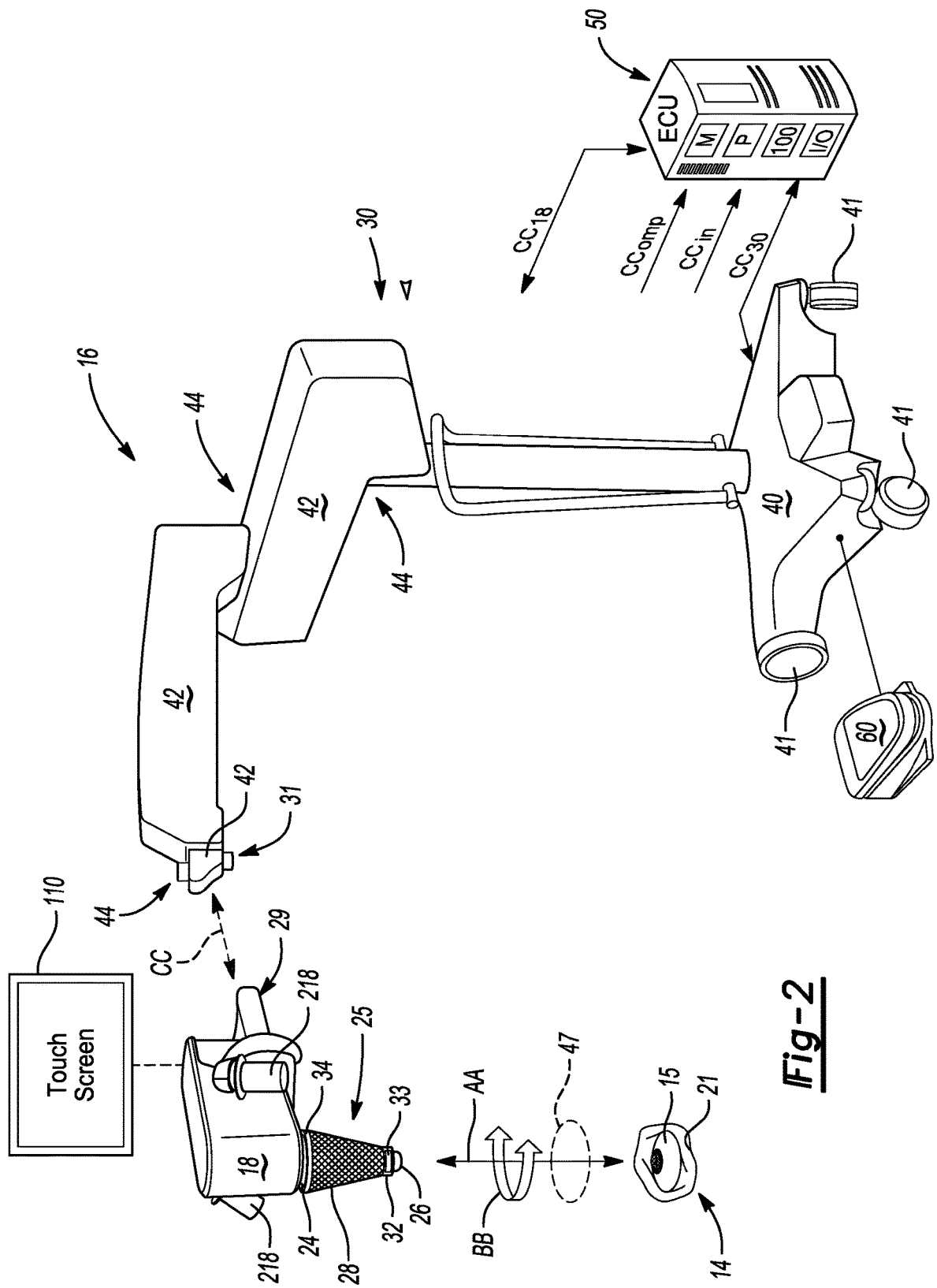
FIG. 2 is a schematic illustration of the retina viewing system shown in FIG. 1.
Figures 3, 4:
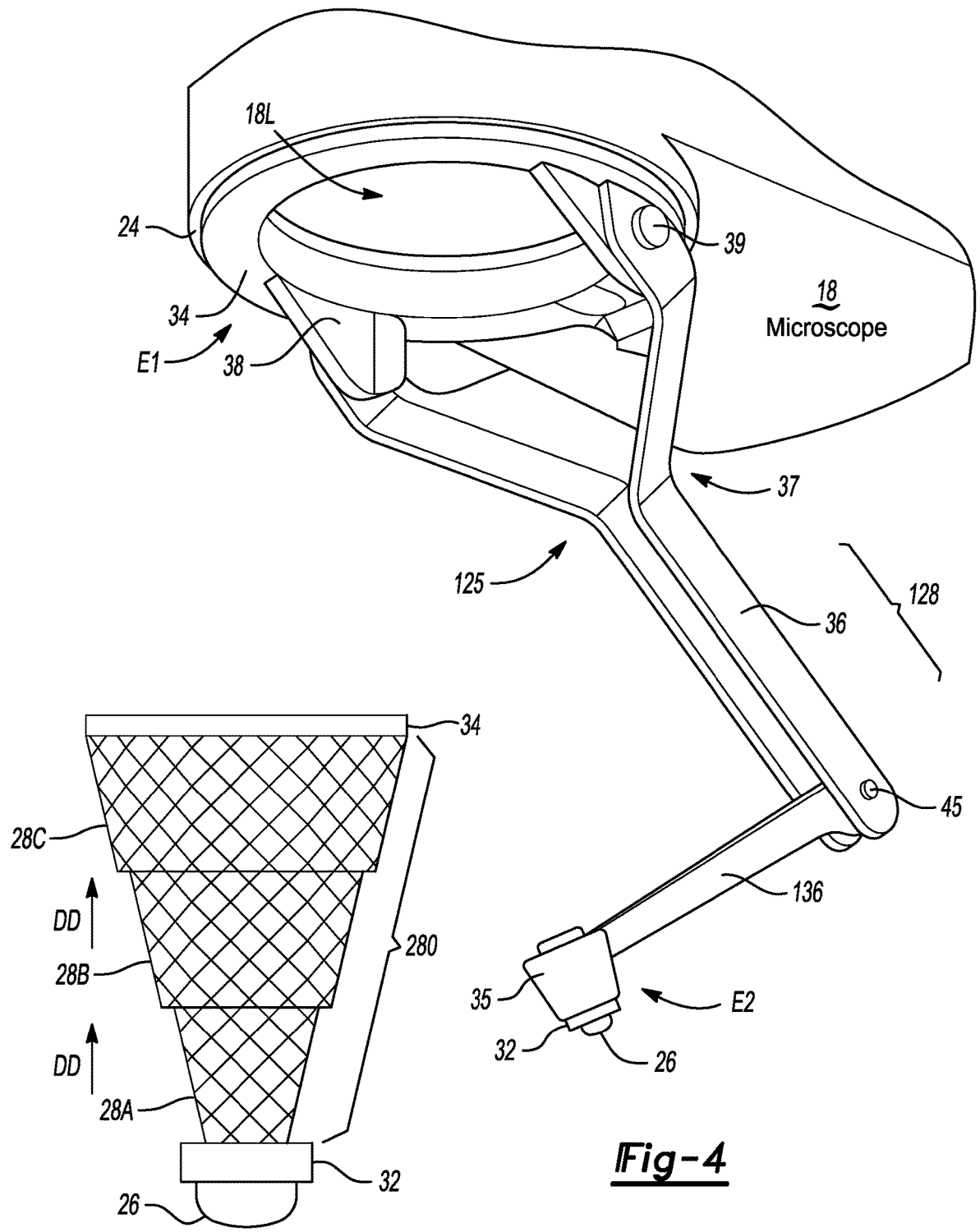
FIG. 3 is a schematic illustration of a telescoping collapsible embodiment of a disposable non-contact lens attachment device usable with the system shown in FIG. 2.
FIG. 4 is a schematic perspective view illustration of an alternative embodiment of the disposable lens attachment device usable with the retina viewing system of FIGS. 1 and 2.

Still referring to FIG. 1, the retina viewing system 16 may be attached to an optical head 24 of the ophthalmic microscope 18 using a mechanical engagement element, such as is depicted in FIG. 3, or via the forces of attraction such as magnetic attraction, a hook-and-loop connection, a friction/ interference fit, or medical grade adhesives as shown in FIGS. 1 and 2. The clinician 12 and/or the multi-axis robot 30 of FIG. 2 may adjust the spatial position and orientation of the microscope 18 relative to a cornea surface of the exposed eye 14. For illustrative clarity, the microscope 18 and a disposable lens attachment 25 connected thereto is shown a greater distance away from an actual operating position, in which a high-power/high-diopter distal lens 26 of the disposable lens attachment 25 is typically positioned about 5 mm-10 mm away from a cornea surface of the eye 14. The need for precise and repeatable positioning of the distal lens 26 relative to the cornea surface thus lends itself to the integrated precision focusing approach of the present disclosure, with an exemplary method 100 for using the retina viewing system 16 once again described below with reference to FIG. 5.

In the course of performing the exemplary ophthalmic procedure 10 of FIG. 1, in some embodiments the clinician 12 may elect to view the retina or other target area of the eye 14 through a set of optical eye pieces (not shown). As appreciated in the art, such eye pieces may be an integral part of certain commercially available medical-grade ophthalmic microscopes to provide the clinician 12 or other attending practitioners with a particular view. Non-limiting exemplary microscopes in this category include the LuxOR® Revalia Ophthalmic Microscope from Alcon, Inc., as well as the OPMI Lumera® 700 from Carl Zeiss Meditec, Inc. Other commercially-available microscopes, such as but not necessarily limited to the Aesculap AEOS™ Digital Microscope from Aesculap, Inc., forego use of such eyepieces. Thus, eye pieces may be present or absent from the construction of the ophthalmic microscope 18 within the scope of the present disclosure.

Control surfaces may be present on a pair of control handles 118 of the ophthalmic microscope 18, with one such control handle 118 visible from the perspective of FIG. 1. Such paddle-like control handles 118 may be alternatively configured as cylindrical bicycle grip-style handles 218 as shown in FIG. 2, or as another suitable shape. Once the ophthalmic procedure 10 is finished, the disposable lens attachment 25 may be quickly and easily detached from the optical head 24 of the microscope 18 and discarded, thereby providing the above-noted low-cost disposable option. A small touchscreen 110 may likewise be used as an additional control input device to an electronic control unit (ECU 50) of FIG. 2 and/or the microscope 18.

With respect to the high-power/high-diopter distal lens 26 used as an integral component of the disposable lens attachment 25, the term "high-power/high-diopter" refers to an application-suitable level of magnification. In a non-limiting example, a refractive power of at least 70 diopters may be desirable, with a range of about 70 diopters to about 110 diopters possibly being optimal for performing certain representative procedures 10, e.g., a vitreoretinal surgery. The distal lens 26 may be aspherical in some embodiments, although this shape is not strictly necessary. For example, the distal lens 26 may be spherical, in which case spherical aberrations may be corrected in software by the ECU 50, using another lens, the microscope 18, etc.

As will be appreciated by those skilled in the art, the distal lens 26 is configured to optically invert light from posterior regions of the vitreous cavity of the eye 14, with such light possibly emitted from within the vitreous cavity via endoillumination. The distal lens 26 thus provides a virtual image of the retina and surrounding tissue. Light passing through the distal lens 26 propagates directly to the ophthalmic microscope 18 in some embodiments, which would have the benefit of eliminating intervening reducing lenses of the type typically used with fixed working distance ophthalmic microscopes as described above. In other embodiments, an optional reducing lens 47 (see FIG. 2) may be used, with such an option providing a different or preferred field of view.

With respect to the variable working distance/focal length capabilities of the ophthalmic microscope 18 contemplated herein for use with the retina viewing system 16 of the present disclosure, the internal focusing lenses 18L provide a variable working distance, for instance about 150 mm to 450 mm in a non-limiting representative embodiment. Ranges falling within these limits may be used in other embodiments, e.g., 150 mm-300 mm or 150 mm-200 mm, with automatic adjustment of the internal focusing lenses 18L occurring directly or indirectly in response to focus control signals (arrow $CC_{18}$) from the ECU 50, as shown in FIG. 2 and described below. The microscope 18 thus directly focuses on the virtual image produced by the distal lens 26.

The disposable lens attachment 25 is securely but temporarily connected to the optical head 24 of the ophthalmic microscope 18 via a connection ring 34 disposed at a proximal end E1 of the disposable lens attachment 25. In the exemplary embodiment of FIGS. 1 and 2, for instance, the disposable lens attachment 25 is constructed from a resilient body 28 that, in the illustrated representative configuration, is conical in shape and forms a bendable and/or collapsible compliant scaffolding. In the event of inadvertent contact between the distal lens 26 and the eye 14, the resilient body 28 is configured to telescope, bend, or otherwise collapse safely away from the eye 14. That is, the resilient body 28 is highly pliable, bendable, and elastically resilient as opposed to being stiff and unyielding. Possible constructions include a soft lightweight molded plastic or silicone rubber, perforated or latticed material, or a network of interlaced horizontal and vertical linkages forming a suspension net, a thin disposable membrane, or another suitable construction, as well as the telescoping configuration of FIG. 3 as described below.

At the proximal end E1 of the disposable lens attachment 25, the connection ring 34 may be potted or otherwise connected to the resilient body 28, e.g., via a cured medical grade adhesive material. The connection ring 34 is configured to securely engage the optical head 24 of the ophthalmic microscope 18, such as via direct engagement (FIG. 3) or solely via magnetic or other forces of attraction (FIGS. 1 and 2), possible alternatives to the latter including hook-and-loop, adhesive materials, and friction/interference fit as noted above. Such forces may be used to advantage to simplify the attachment and disconnection process, with connection possibly aided by structural alignment features on the microscope 18 and/or the connection ring 34 that collectively allow the connection ring 34 to securely lock into place with respect to the optical head 24.

At a distal end E2 of the disposable lens attachment 25, i.e., diametrically opposite the proximal end E1/connection ring 34, a small protective sleeve 32 constructed of an opaque medical grade polymer or metal material may be disposed between the distal lens 26 and the resilient body 28 to help reduce glare on the distal lens 26, as well as to facilitate a secure connection of the distal lens 26 to the resilient body 28. While other shapes and/or structural configurations of the resilient body 28 are possible within the scope of the disclosure, the depicted conical shape may help prevent an intrusion of dust or debris on the distal lens 26 from above, i.e., from the direction of the ophthalmic microscope 18.

Referring briefly to FIG. 3, the resilient body 28 may optionally include a telescoping plurality of resilient bodies 280, i.e., resilient bodies 28A, 28B, and 28C. The resilient bodies 280 are collectively configured to articulate or pivot with respective to other and thus collapse away from the patient eye 14 in response to contact therewith. That is, with distal lens 26 attached to the smallest diameter one of the resilient bodies 280, i.e., resilient body 28A, any contact with the eye 14 would cause the resilient body 28A to move upward into the slightly larger diameter resilient body 28B, which in turn is urged into the resilient body 28C in a telescoping manner, as indicated by arrows DD. Absent contact with the eye 14, forces of gravity would cause the resilient bodies 280 to return to the equilibrium position depicted in FIG. 3.

As shown in FIG. 4, the disposable lens attachment 25 of FIG. 1 may be alternatively embodied as a disposable lens attachment 125 having another resilient body 128. As shown, the resilient body 128 is an articulated mechanism having a plurality of hinged arm segments, shown as respective first and second arm segments 36 and 136. The first arm segment 36 is configured to mechanically engage the optical head 24 of the ophthalmic microscope 18 at the proximal end E1, e.g., via fasteners 39 and tabular extensions 38.

In the illustrated configuration, the first arm segment 36 defines a Y-shaped or forked end 37 which opens to receive the tabular extensions 38 and fasteners 39. Additional fasteners 45 may connect the second arm segment 136 to the first arm segment 36, such that fasteners 45 form pivot points allowing the second arm segment 136 to rotate about the axis of the fastener 45 so as to raise or lower the distal lens 26 that is disposed at the distal end E2. In this embodiment, a support member 35 such as a cylindrical or generally conical metal or plastic may be used to provide a suitable mass for connecting the distal lens 26 and the protective sleeve 32 to the distal end E2.

Referring now to FIG. 2, the above-described ophthalmic microscope 18 may be optionally coupled to an end-effector 31 of the multi-axis robot 30 noted briefly above, with such coupling indicated via double-headed arrow CC. As appreciated, such a robot 30 typically includes a base 40 connected to a set of wheels 41. To provide multiple degrees of freedom of movement, the robot 30 is equipped with a plurality of linkages 42, with the various linkages 42 being interconnected via corresponding revolute joints 44. The base 40 may be connected to the wheels 41 to facilitate relocation or movement of the robot 30 within a facility or a given surgical suite.

Within the construction of the robot 30, therefore, each revolute joint 44 may be actively driven in some embodiments by a rotary actuator (not shown), e.g., a servo motor, to provide multiple control degrees of freedom, including forward/backward, vertical, and horizontal translation as well as pitch, yaw, and roll orientation of the end-effector 31. Other embodiments may enable the clinician 12 to passively reposition the robot 30 without the aid of such actuators. Collectively, the revolute joints 44 and the various linkages 42 allow the end-effector 31 and components of the retina viewing system 16 connected thereto to move, or to be moved, within a defined workspace. In this manner, the robot 30 is able to facilitate precise positioning of the distal lens 26 relative to a cornea surface 15 of the eye 14, as indicated by arrows AA and BB.

As shown in FIG. 2, motion control of the ophthalmic microscope 18 and the connected retina viewing system 16 may be commanded by the clinician 12 of FIG. 1 using different control inputs. For example, to command the robot 30 to position the optical head 24 at a particular orientation and spatial position in a three-dimensional Cartesian frame of reference, the clinician 12 could depress a foot pedal 60 and/or activate a keypad (not shown) disposed on the control handles 118 or 218 of the ophthalmic microscope 18, with the latter configuration depicted in FIG. 2. Additional control inputs may be entered via the touch screen 110.

Software programming for the robot 30 may in some embodiments automatically identify the eye 14, e.g., using a machine vision algorithm, a neural network, proximity sensing, etc., and thereafter automatically position and orient the retina viewing system 16, and in particular the distal lens 26 thereof, a predetermined distance away from the cornea surface 15, typically about 5-10 mm away as appreciated in the art. Such software can therefore communicate with resident control logic of the ophthalmic microscope 18 to automatically adjust the working distance/focal length of the internal focusing lenses 18L thereof without required intervention by the clinician 12.

Additionally, using control inputs from the foot pedal 60, the control handles 118 or 218, and/or the touchscreen 110 mounted near or on the retina viewing system 16, the clinician 12 is able to turn on the light 70 (see FIG. 1) on the underside 29 of the ophthalmic microscope 18 to cause the microscope 18 to emit the above-noted light beam LL, or to automatically retract the optical head 24 by a predetermined distance, e.g., 50-75 mm, and/or to remove the retina viewing system 16 from view when working on the anterior portion of the eye 14. When the clinician 12 is ready to return to a posterior view, the clinician 12 could simply click the retina viewing system 16 into place on the optical head 24 and thereafter use the same control inputs.

Using position sensing, machine vision, and/or artificial intelligence of the type noted above, the ophthalmic microscope 18, controlled in some respect via the ECU 50, could automatically detect the retina viewing system 16 or otherwise determine that the retina viewing system 16 has been successfully mounted to the optical head 24. Machine vision could likewise be used to detect the retina viewing system 16 being attached or detached. In response, the ECU 50 may command the robot 30 to move the microscope 18 up or down, and/or position the distal lens 26 at the preset 5-10 mm distance above the cornea 15. Without an external focus input or any other input being required from the clinician 12, optional auto-focus control/adjustment of the internal focusing lenses 18L by the ECU 50 as part of the method 100 shown in FIG. 5 could thus be used to obtain the proper focus so that the clinician 12 is ready to attend to the operation.

The retina viewing system 16 of the present disclosure is intended to be single-use, and thus is configured to be disposable. To that end, a serialization strategy may be enforced by the ECU 50 to protect against inadvertent reuse of a given retina viewing system 16. Such a strategy may be facilitated by existing CMOS or other cameras of the ophthalmic microscope 18. For example, a scannable bar code, QR code, or other unique serial identifier code 33 may be printed on, adhered to, or otherwise incorporated into the retina viewing system 16 and/or its hermetically sealed packaging (not shown) to log usage and prevent reuse. Exemplary locations for imprinting the serial identifier code 33 include the connection ring 34, which from a top view may provide a sufficiently wide and planar surface for printing or attaching a label containing the serial identifier code 33, or a surface of the protective sleeve 32. Other approaches such as RFID tags may be used in other embodiments.

To enable the various software-based control aspects of the present disclosure, the ECU 50 is in networked communication with the ophthalmic microscope 18 and the robot 30, with such two-way communication indicated by double-headed arrow $CC_{30}$ in FIG. 2. The ECU 50 may be configured to execute computer-readable code or instructions embodying the method 100 for performing one or more tasks involving use of the retina visualization system, with an exemplary embodiment of the method 100 depicted in FIG. 5 and described below. Although the ECU 50 is shown schematically as a unitary device for illustrative simplicity, the ECU 50 may include one or more networked computer devices, along with associated computer-readable media or memory (M), including a non-transitory (e.g., tangible) medium that participates in providing data/instructions that may be read by one or more processors (P).

The memory (M) may take many forms, including but not limited to non-volatile media and volatile media. As will be appreciated, non-volatile media may include optical and/or magnetic disks and other persistent memory, while volatile media may include dynamic random-access memory (DRAM), static RAM (SRAM), etc., any or all which may constitute a main memory. Communication with the ophthalmic microscope 18 and the robot 30 may be achieved via a networked connection to input/output (I/O) circuitry of the ECU 50. Other hardware not depicted but well established in the art may be included as part of the ECU 50, including but not limited to a local oscillator or high-speed clock, signal buffers, digital signal filters, etc.

Figure 5:
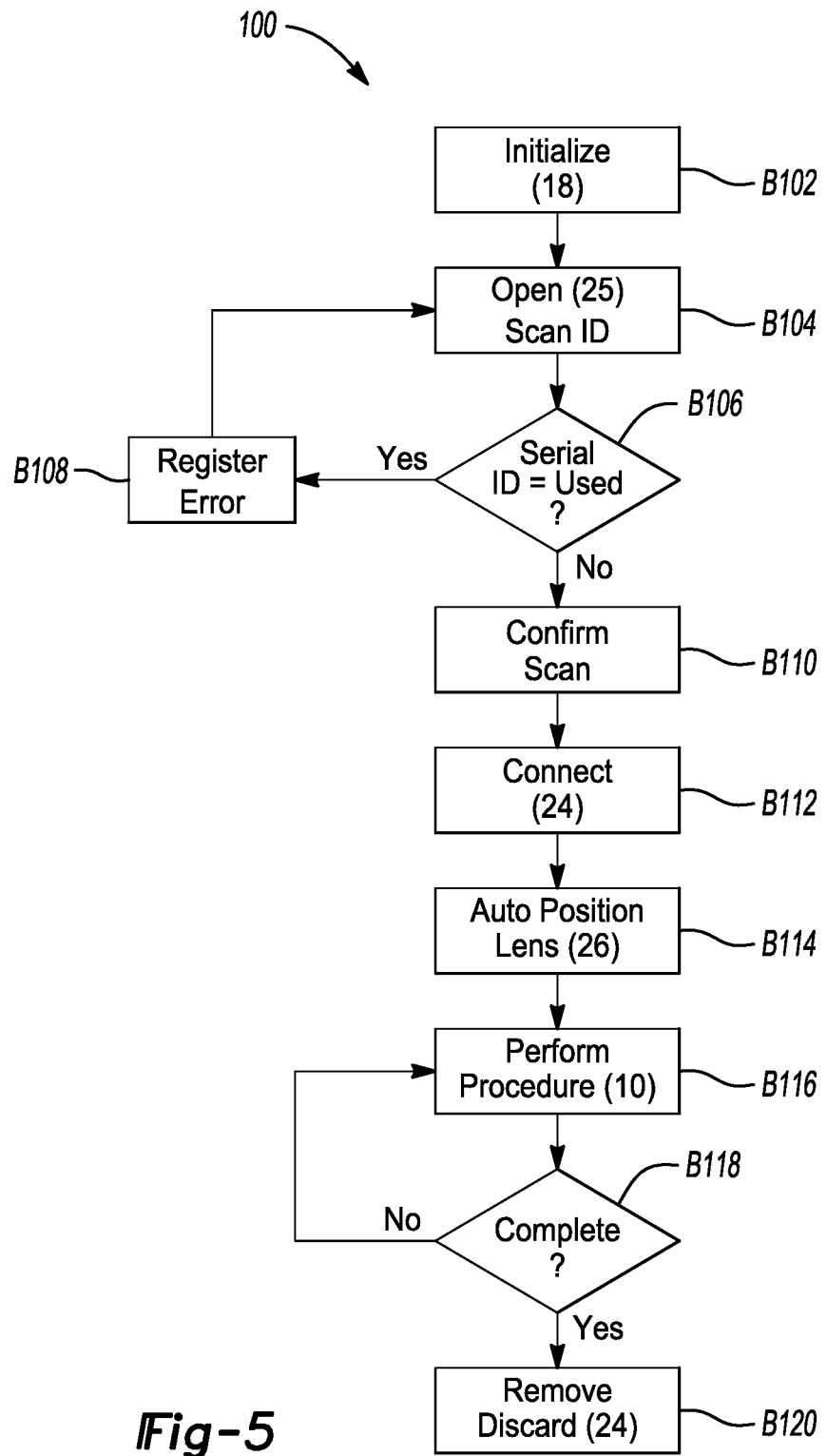
FIG. 5 is a flow chart describing a representative embodiment of a method for using the retina viewing system of FIG. 2.

Referring to FIG. 5, the method 100 noted above in an exemplary embodiment may commence at sequential block B102 with initialization of the retina viewing system 16. For example, the clinician 12 may turn on the robot 30 and the ophthalmic microscope 18 in preparation for the ophthalmic procedure 10 shown in FIG. 1. Block B102 may entail coarse automatic or manual positioning of the robot 30 and the microscope 18 relative to an operating position to be occupied by the patient 140 of FIG. 1. Initialization may result in receipt of an initiation signal (arrow $CC_{IN}$) by the ECU 50, which could ultimately respond by prompting for connection of the disposable lens attachment 25 or 125 to the optical head 24 as set forth below. The method 100 proceeds to block B104 after initialization is complete.

At block B104, the clinician 12 opens a hermetically sealed package containing the above-described disposable lens attachment 25 of FIGS. 1-3 or the alternative disposable lens attachment 125 of FIG. 4. As part of the method 100 of FIG. 5, the package and/or the disposable lens attachment 25 or 125 may include a unique serial identifier code 33. In such an embodiment, the clinician 12 may scan the serial identifier code 33 to thereby log the usage of the disposable lens attachment 25 or 125 in memory (M) or a database. In a possible embodiment, onboard CMOS cameras or other onboard optical scanning capabilities of the ophthalmic microscope 18 may be used to scan the serial identifier code 33 as a scanned input, in which case the microscope 18 could transmit the scanned input to the ECU 50, or scanning may be achieved using an external scanning device. The method 100 then proceeds to block B106.

At block B106, the ECU 50 compares the serial identifier code from block B104 as a scanned input to a preloaded list of previously used identifier codes. Such a list may be stored or prepopulated in the memory (M) of the ECU 50, for instance in a lookup table. Each time a clinician 12 opens and scans a respective serial identifier code 33 for a respective disposable lens attachment 25 or 125, the serial identifier code is recorded in memory (M) for later comparison. The method 100 proceeds to block B108 when the serial identifier code appears on the preloaded list, and to block B110 in the alternative when the serial identifier code does not appear on the preloaded list.

At block B108, as a control action the ECU 50 may register/record an error code in memory (M) that is indicative of the prior use of the disposable lens attachment 25 or 125, and thereafter activating an audio and/or visual indicator via the ECU 50. That is, responsive to recording the error code, the ECU 50 may alert the clinician 12 that the disposable lens attachment 25 or 125, or at least its associated serial identifier code, has been previously used. For instance, the ECU 50 may illuminate a red light or other visual indicator, or may display a corresponding message on the display screen 11 and/or 110 of FIGS. 1 and 2, and/or activate an audible alarm indicative of the prior use of the disposable lens attachment 25. The method 100 then repeats block B104.

Block B110 includes confirming the scan result from block B104, e.g., by recording a bit code indicative of no prior use of the disposable lens attachment 25 or 125, via the ECU 50, with this control action possibly followed by a confirmation signal. For instance, the ECU 50 may automatically activate an audio and/or visual indicator as a control action, such as by illuminating a green light or other visual indicator device on the display monitor 11, the touch screen 110, and/or a separate device. The ECU 50 may also display a corresponding message on the display monitor 11 and/or touch screen 110 of respective FIGS. 1 and 2, and/or activate an audible chime or tone indicative of no detected prior use of the disposable lens attachment 25 or 125.

Block B110 thus includes automatically verifying proper connection of the proximal end E1 of the disposable lens attachment 25 or 125 to the optical head 24 of the ophthalmic microscope 18, such as using machine vision capabilities to discern accurate positioning and/or by receiving a confirmation signal (arrow $CC_{IN}$) from a control panel indicative of the proper connection. Such confirmation would occur in conjunction with a bit code indicating no prior use of the disposable lens attachment 25 or 125, with the control panel possibly including the above-described control handles 118 or 218, the touch screen 110, etc. The method 100 then proceeds to block B112.

Block B112 entails connecting the disposable lens attachment 25 or 125 to the optical head 24 of the ophthalmic microscope 18. Block B112 may include placing the disposable lens attachment 25, in the FIG. 1 and FIG. 2 embodiment, adjacent to the optical head 24 and allowing the forces of magnetic attraction from the magnetic connection ring 34, or hook-and-loop attraction or forces of friction or adhesion, to secure the disposable lens attachment 25 in place. In the alternative embodiment of FIG. 4, the disposable lens attachment 125 may be mechanically coupled to the optical head 24. The method 100 then proceeds to block B114.

Block B114 includes commencing the ophthalmic procedure 10 of FIG. 1. In a possible embodiment, block B114 may include inputting an initiation signal to the ECU 50 indicative of a desire of the clinician 12 to begin the procedure 10. In response, the ECU 50 may automatically command the robot 30 of FIG. 2 to position the disposable lens attachment 25 or 125, and in particular the distal lens 26 thereof, at the predetermined distance of about 5-10 mm away from the cornea surface 15 of the eye 14 shown in FIG. 2.

Once so positioned, the ECU 50 may then adjust the variable working distance or focal length of the ophthalmic microscope 18 via direct auto-focusing control of its internal focusing lenses 18L, or via a motor-driven response to inputs from the clinician 12. That is, the control response by the ECU 50 relative to the focal setting of the microscope 18 may occur fully autonomously or only in response to input signals from a clinician input device, e.g., the foot pedal 60, control handles 118 or 218, or the touch screen 110. This enables the clinician 12 to view an image of a retina or other intraocular structure of the patient eye 14 through the distal lens 26 using the microscope 18. The method 100 thereafter proceeds to block B116.

At block B116, the clinician 12 performs the ophthalmic procedure 10 until its completion. Inputs to the ECU 50 during the course of the procedure 10 may be provided via the control handles 118 or 218 of FIGS. 1 and FIG. 2, respectively, the touch screen 110 and/or the foot pedal 60 of FIG. 2, etc., with the ECU 50 reacting by transmitting corresponding position control signals (arrow $CC_{30}$) to the robot 30. The method 100 proceeds to block B118 when the corresponding position control signals (arrow $CC_{30}$) have been transmitted to the robot 30.

Block B118 may include determining whether the ophthalmic procedure 10 is complete. For example, upon completion of the procedure 10 the ECU 50 may receive a completion signal (arrow $CC_{COMP}$ of FIG. 2) indicative of a desire of the clinician 12 to end the procedure 10. In various embodiments, generation of the completion signal may result when the clinician 12 touches a corresponding "end procedure" icon on the display screen 110, or when the clinician 12 moves or commands movement of the ophthalmic microscope 18 a predetermined distance away from the patient 140. In response to either input, the ECU 50 may activate some or all of the revolute joints 44 of the robot 30 to assist in the relocation of the ophthalmic microscope 18. The method 100 then proceeds to block B120.

Block B120 entails removing the disposable lens attachment 25 or 125 from the optical head 24. The clinician 12 can then discard the disposable lens attachment 25 or 125. The method 100 is then complete, beginning anew at block B102 for a subsequent ophthalmic procedure 10.

The retina viewing system 16 described herein therefore provides a lower-cost, non-contact, wide-angle retina viewing option. Simplified utility is provided by virtue of eliminating the need for the surgeon 12 to externally focus the ophthalmic microscope 18. That is, by configuring the microscope 18 and via programming of the ECU 50 to place the virtual image from the distal lens 26 within the variable working distance of the microscope 18, the present solution eliminates the need to externally focus via intervening reducing lenses. As will be appreciated by those skill in the art, elimination of the external focus control requirement shortens the length of the ophthalmic procedure 10. This in turn, taken in conjunction with the reuse-preventing serialization strategies presented above, may help reduce the overall risk of surgical complications. These and other attendant benefits will be readily appreciated by those of ordinary skill in the art in view of the foregoing disclosure.

The detailed description and the drawings are intended to be supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A retina viewing system comprising:
   an ophthalmic microscope having an optical head and a set of internal focusing lenses, the set of internal focusing lenses providing the ophthalmic microscope with a variable working distance or focal length;
   a disposable lens attachment having a resilient body and a high-power/high-diopter distal lens, wherein a proximal end of the disposable lens attachment is connected to the optical head, and a distal end of the disposable lens attachment is connected to the distal lens;
   wherein the resilient body of the disposable lens attachment is constructed of a flexible material configured to bend and collapse away from a patient eye in response to contact therewith; and
   an electronic control unit (ECU) in communication with the ophthalmic microscope and programmed to execute instructions for viewing a retina of a patient eye, wherein execution of the instructions by a processor of the ECU causes the ECU to focus the internal focusing lenses, autonomously or in response to input signals from a clinician input device, to thereby adjust the variable working distance or focal length of the ophthalmic microscope when viewing an image of the retina through the distal lens.

2. The retina viewing system of claim 1, further comprising:
   a multi-axis robot in communication with the ECU, wherein execution of the instructions by the processor causes the multi-axis robot to automatically position the ophthalmic microscope such that the distal lens is a predetermined distance away from a cornea surface of the patient eye.

3. The retina viewing system of claim 1, wherein the resilient body of the disposable lens attachment has a conical shape.

4. The retina viewing system of claim 3, wherein the resilient body includes a telescoping plurality of resilient bodies collectively configured to pivot relative to one another and collapse away from the patient eye in response to contact therewith.

5. The retina viewing system of claim 1, wherein the disposable lens attachment includes a magnetic connection ring forming the proximal end of the resilient body, and wherein the disposable lens attachment is magnetically connected to the optical head of the ophthalmic microscope solely via the magnetic connection ring.

6. The retina viewing system of claim 1, wherein the distal lens has a refractive power level of 70 diopters to 110 diopters.

7. The retina viewing system of claim 1, wherein a surface of the disposable lens attachment is imprinted with a unique serial identifier code configured to prevent reuse of the disposable lens attachment.

8. The retina viewing system of claim 7, wherein to prevent the reuse of the disposable lens attachment, the ECU is configured to:
   receive a scanned input of the serial identifier code; and in response to the scanned input matching a previously recorded serial identifier code, to execute a control action preventing the reuse of the disposable lens attachment.

9. The retina viewing system of claim 8, wherein the ophthalmic microscope is configured to automatically scan the serial identifier code to generate the scanned input, and to thereafter transmit the scanned input to the ECU.

10. The retina viewing system of claim 1, further comprising:
a protective sleeve disposed between the distal lens and the resilient body.

11. A method for controlling a retina viewing system during an ophthalmic procedure on a patient eye, the method comprising:
in response to receiving an initiation signal by an electronic control unit (ECU), automatically verifying a connection of a proximal end of a disposable lens attachment to an optical head of an ophthalmic microscope, wherein the ophthalmic microscope includes a set of internal focusing lenses providing the ophthalmic microscope with a variable working distance or focal length, and wherein a distal end of the disposable lens attachment is connected to a high-power/high-diopter distal lens; and
in response to verifying the connection of the proximal end, automatically adjusting the variable working distance or focal length of the ophthalmic microscope via the ECU, autonomously or in response to input signals from a clinician input device, to thereby view an image of a retina of the patient eye through the distal lens using the ophthalmic microscope.

12. The method of claim 11, wherein the ECU is in communication with a multi-axis robot, the method further comprising, while the ophthalmic microscope is coupled to an end-effector of the multi-axis robot:
automatically positioning the ophthalmic microscope and the disposable lens attachment via transmission of position control signals to the multi-axis robot by the ECU, such that the distal lens is 5 mm to 10 mm away from a cornea surface of the patient eye.

13. The method of claim 11, wherein automatically verifying the connection of the proximal end of the disposable lens attachment includes receiving a confirmation signal from a control panel indicative of the connection via the ECU.

14. The method of claim 11, wherein the disposable lens attachment is imprinted with a unique serial identifier code, the method further comprising:
receiving a scanned input of the unique serial identifier code via the ECU; and
executing a control action in response to the scanned input matching a previously recorded serial identifier code, wherein the control action is directed toward preventing reuse of the disposable lens attachment.

15. The method of claim 14, further comprising: scanning the identifier code via the ophthalmic microscope to generate the scanned input, and thereafter transmitting the scanned input to the ECU.

16. The method of claim 14, wherein executing the control action includes registering or recording an error code in memory of the ECU that is indicative of a prior use of the disposable lens attachment, and thereafter activating an audio and/or visual indicator via the ECU.

17. A disposable lens attachment for use with a retina viewing system having an ophthalmic microscope with an optical head, the disposable lens attachment comprising:
a high-power distal lens having refractive power of 70 diopters to 110 diopters; and
a conical resilient body having a proximal end configured to connect to the optical head of the ophthalmic microscope, and a distal end connected to the distal lens, wherein the conical resilient body is constructed of a resilient material configured to bend and collapse away from a patient eye in the event of contact therewith.

18. The disposable lens attachment of claim 17, wherein the conical resilient body is constructed of a flexible perforated or latticed material and includes a perforated wall.

19. The disposable lens attachment of claim 17, further comprising: a magnetic connection ring connected to the conical resilient body, and configured to magnetically connect to the optical head solely via the magnetic connection ring.

20. The disposable lens attachment of claim 19, wherein the magnetic connection ring is imprinted with a unique serial identifier code configured to prevent reuse of the disposable lens attachment.

* * * * *